(12) United States Patent
Kroon et al.

(10) Patent No.: US 9,939,075 B2
(45) Date of Patent: Apr. 10, 2018

(54) MANIFOLD DRIVER

(71) Applicant: BIOCARTIS NV, Mechelen (BE)

(72) Inventors: Gerard Kroon, Eindhoven (NL); Ronald De Gier, Eindhoven (NL)

(73) Assignee: BIOCARTIS NV, Mechelen (BE)

( * ) Notice: Subject to any disclaimer, the term of this patent is extended or adjusted under 35 U.S.C. 154(b) by 11 days.

(21) Appl. No.: 14/783,582

(22) PCT Filed: Apr. 11, 2014

(86) PCT No.: PCT/EP2014/057412
§ 371 (c)(1),
(2) Date: Oct. 9, 2015

(87) PCT Pub. No.: WO2014/167109
PCT Pub. Date: Oct. 16, 2014

(65) Prior Publication Data
US 2016/0069464 A1    Mar. 10, 2016

(30) Foreign Application Priority Data
Apr. 12, 2013  (EP) ..................... 13163554

(51) Int. Cl.
*F16K 27/04* (2006.01)
*B01L 3/00* (2006.01)
(Continued)

(52) U.S. Cl.
CPC ........ *F16K 27/04* (2013.01); *B01L 3/502715* (2013.01); *F16K 3/0218* (2013.01);
(Continued)

(58) Field of Classification Search
CPC ............... F16K 27/04; B01L 3/502715; B01L 2400/0644
(Continued)

(56) References Cited

U.S. PATENT DOCUMENTS

| 3,273,595 A * | 9/1966 | Novak ..................... F16K 5/10 |
| | | 137/597 |
| 3,612,104 A * | 10/1971 | Busquets .............. F16K 11/202 |
| | | 137/597 |
| 4,653,537 A * | 3/1987 | Voith .................. F16K 11/0836 |
| | | 137/625.43 |
| 4,689,204 A | 8/1987 | Buck et al. ................... 422/100 |

(Continued)

FOREIGN PATENT DOCUMENTS

WO    WO 2009/087857    7/2009 ............ G01N 35/05

OTHER PUBLICATIONS

International Search Report from corresponding International Patent Application No. PCT/EP2014/057412, dated Jul. 25, 2014.
(Continued)

*Primary Examiner* — Reinaldo Sanchez-Medina
(74) *Attorney, Agent, or Firm* — Kusner & Jaffe

(57) ABSTRACT

A fluid control and processing system comprising a cartridge and an instrument for operating the cartridge. The cartridge comprises a cylinder body comprising a cylinder and a fluid port. It further comprises dispensing ports to drive a fluid flow, each dispensing port being positioned to be connectable, when the instrument is operating the cartridge, with at least a fluid port by rotation of the cylinder body. The instrument comprises a piston driver for driving the piston. The system further comprises: reversible fastening means for fastening the piston when the piston driver is rotated with respect to the piston, so that the movement of the piston is controlled by the piston driver; and rotating means comprising a cylinder driver constitutive of the instrument for rotating the cylinder body around the axis A.

11 Claims, 5 Drawing Sheets

(51) Int. Cl.
*G01N 35/00* (2006.01)
*G01N 35/10* (2006.01)
*F16K 3/02* (2006.01)
*F16K 3/30* (2006.01)

(52) U.S. Cl.
CPC ........... *F16K 3/30* (2013.01); *G01N 35/0099* (2013.01); *G01N 35/1009* (2013.01); *B01L 2200/025* (2013.01); *B01L 2200/027* (2013.01); *B01L 2200/04* (2013.01); *B01L 2300/049* (2013.01); *B01L 2300/087* (2013.01); *B01L 2300/0809* (2013.01); *B01L 2300/0832* (2013.01); *B01L 2400/0478* (2013.01); *B01L 2400/0644* (2013.01)

(58) Field of Classification Search
USPC ............ 137/315.17, 315.27, 315.21, 315.35, 137/315.36, 315.41, 343, 625.46, 625.47, 137/637, 637.1, 637.2, 637.3, 637.4
See application file for complete search history.

(56) References Cited

U.S. PATENT DOCUMENTS

| | | |
|---|---|---|
| 6,656,428 B1 | 12/2003 | Clark et al. ..................... 422/58 |
| 8,048,386 B2 | 11/2011 | Dority et al. .................. 422/500 |
| 8,171,958 B2* | 5/2012 | Morreale .................. F16K 3/24 |
| | | 137/614.16 |
| 8,905,075 B2* | 12/2014 | Tower ....................... F16K 3/08 |
| | | 137/625.15 |
| 2011/0059834 A1 | 3/2011 | Eberle ............................... 494/7 |
| 2012/0183956 A1 | 7/2012 | Ross et al. ..................... 435/6.1 |
| 2012/0325334 A1* | 12/2012 | De Gier ............ B01L 3/502738 |
| | | 137/315.01 |

OTHER PUBLICATIONS

Extended European Search Report from corresponding European Patent Application No. 13163554.2, dated Sep. 9, 2013.

* cited by examiner

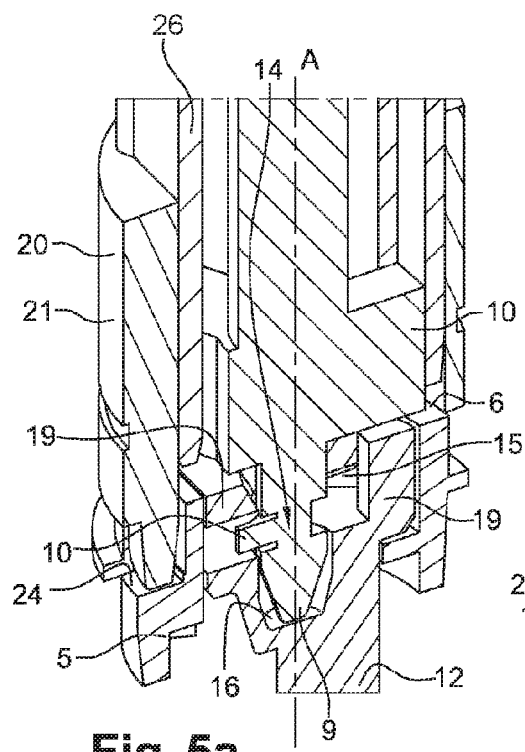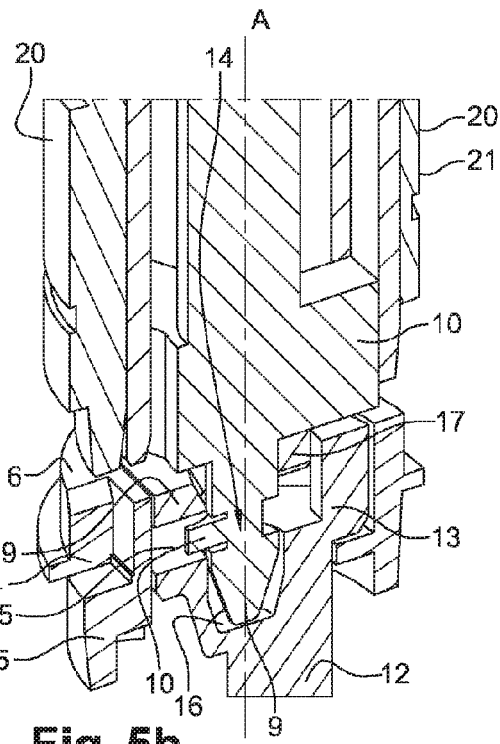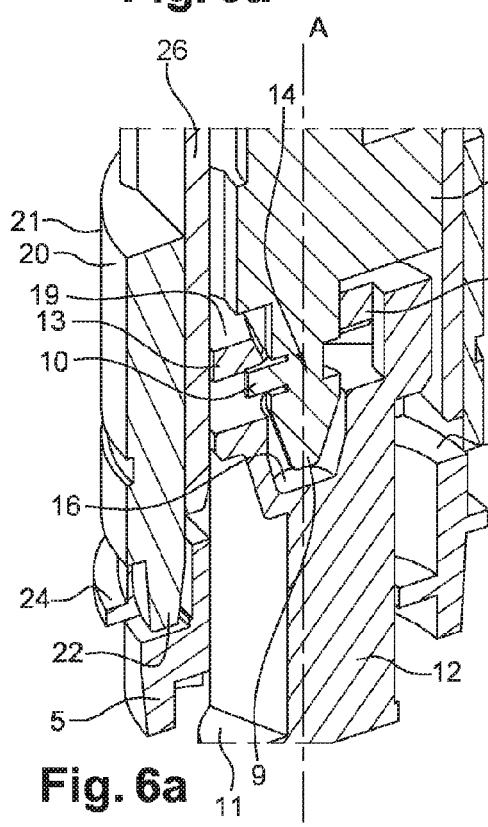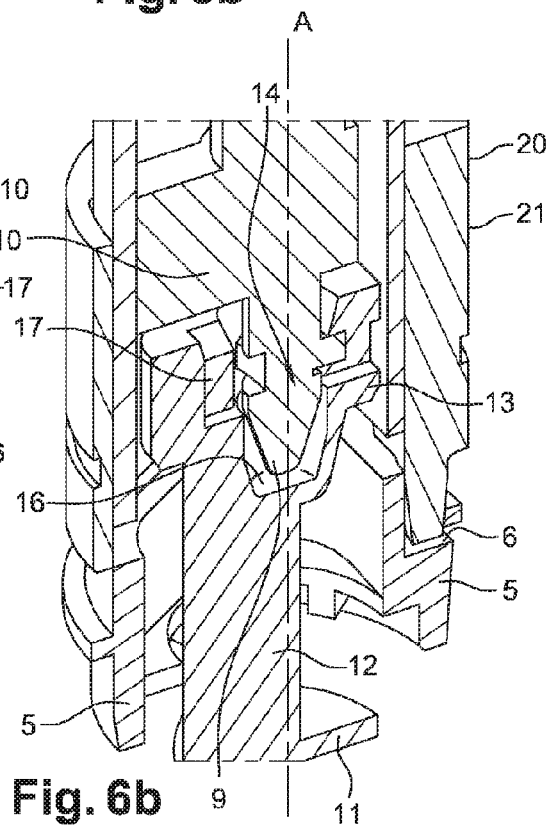

MANIFOLD DRIVER

FIELD OF THE INVENTION

The present invention relates to a fluid control and processing system comprising a cartridge and an instrument designed for operating the cartridge.

BACKGROUND OF THE INVENTION

Analysis of environmental or clinical fluids usually involves multiple step processes, from chemical to thermal or acoustical treatments of the sample. Such protocols are sometimes performed in disposable cartridges that involve microfluidic processes and that comprise for these purposes different inner parts such as fluid containers, reaction chambers, fluid analyzers, microchannels, etc. . . . The movement of the fluids, reagents and liquefied samples, between the different inner parts requires fluid pumps and/or valves. These pumps and/or valves are either enclosed in instruments that are designed for receiving and operating said cartridges or are embedded in the cartridges. The pumps and or valves embedded in an instrument that controls the cartridges present several drawbacks, such as risks of fluid cross contaminations, leakages and wear.

A pump or valve embedded in a disposable cartridge, as described in the document U.S. Pat. No. 8,048,386, usually comprises a plunger and a cylinder for delivering fluids to a rotary port that can be put in fluid communication with one or more channels, each connected to a specific inner part of the cartridge. The interface between such a cartridge and an instrument that operate it is complex and present several drawbacks with respect to accuracy and reliability.

The existing cartridges and instruments do not offer satisfying solutions with respect to the control of the pumps and/or valves and there is a need for cartridges and instruments that offer a simple, accurate and reliable fluid control.

SUMMARY OF THE INVENTION

The present invention aims to remedy all or part of the disadvantages mentioned above. In particular, the present invention aims at providing a fluid control and processing system that is simple, reliable, accurate and avoids contamination of the instrument.

The present invention fulfills these objectives by providing a fluid control and processing system comprising:
  a cartridge;
  an instrument being designed for operating the cartridge;
  at least a cylinder body being received in the cartridge, said at least a cylinder body comprising a cylinder and at least a fluid port in fluid communication with said cylinder;
  a piston being movable in the cylinder to modulate a fluid volume inside said cylinder;
  the fluid control and processing system further comprising dispensing ports to drive at least a fluid flow, each dispensing port being positioned to be connectable, when the instrument is operating the cartridge, with at least a fluid port by rotation of the cylinder body;
  the instrument comprising a piston driver, said piston driver being designed for driving the piston;
  Characterized in that the fluid control and processing system further comprises:
  reversible fastening means for fastening the piston to the piston driver when the piston driver is rotated with respect to the piston in a first direction around an axis A which extends along the piston driver; and said reversible fastening means being designed for unfastening the piston from the piston driver when the piston driver is rotated with respect to the piston in a second direction opposite to the first direction, so that the movement of the piston is controlled by the piston driver;
  rotating means comprising a cylinder driver constitutive of the instrument for rotating the cylinder body around the axis A.

The present invention also relates to a cartridge comprising at least a piston, said cartridge being designed for being used in a fluid control and processing system according to the present invention.

Furthermore, the present invention concerns also an instrument comprising a piston driver, said instrument being designed for being used in a fluid control and processing system according to the present invention.

Thus, the fluid control and processing system according to the present invention solves the technical issues mentioned above by providing reversible fastening means for fastening the piston to the piston driver. Indeed, the piston and the piston driver can be bound together, when the instrument is operating the cartridge, so that the piston driver from the instrument can control the movement of the piston received in the cylinder body of the cartridge. When the piston driver is fastened to the piston via the reversible fastening means, the piston is movable around an axis A extending along the piston driver. Thus, in the system according to the present invention the piston driver can control the movement of the piston both in rotation and in translation around a single axis A. If the cartridge comprises a plurality of cylinder bodies, each cylinder body comprising a cylinder and a piston movable in said cylinder, each piston is movable around the axis extending along the piston driver fastened to the piston received in each cylinder. Thus, the instrument operating the cartridge is capable of modulating individually the fluid volume inside each cylinder by moving the piston around the axis extending along the piston driver fastened to said piston received in each cylinder. Moreover, the rotating means for rotating the cylinder body in respect with the cartridge allow the control of the position of the fluid port with respect to the dispensing ports. The fluid control and processing system according to the present invention further offers flexibility since several cartridges can be operated successively by a given instrument as the fastening means are reversible and therefore allow the piston of the cartridge and the piston driver of the instrument to be unfastened.

According to an embodiment of the present invention, the fastening means comprise at least two parts, a first part and a second part, the piston being attached to said first part and the piston driver comprising said second part.

In an embodiment of the present invention, the rotating means comprise at least a cylinder driver constitutive of the instrument, the cylinder driver being designed for forming a revolute joint with the cylinder body.

According to an embodiment of the invention, the fastening means are designed for fastening the piston with the piston driver when the piston driver is rotated with respect to the piston in a first direction; and are designed for unfastening the piston from the piston driver when the piston driver is rotated with respect to the piston in a second direction opposite to the first direction. Thus, when cartridge is operated by the instrument, a rotation in the first direction of the piston driver with respect to the piston permits the fastening of the cartridge with the instrument via the fastening means; a subsequent translation of the piston driver permits the control of the piston. The rotation in the opposite direction of the piston driver with respect to the piston permits to uncouple the cartridge and the instrument. Such fastening means hence offer flexibility. Such fastening means do not require complex mechanisms.

In an embodiment of the present invention, the fastening means comprise a bayonet mount. Such a bayonet mount is simple and requires a limited number of technical parts. With such a bayonet mount, the coupling and uncoupling are swift and require rotating the piston driver by a low angle.

In an embodiment, the fluid control and processing system further comprises interlocking means for interlocking the piston driver and the rotating means, so that the rotation of the cylinder body is controllable by the piston driver, when the piston driver and the piston are fastened by the fastening means. It is critical for the connection between the cartridge and the instrument according to the invention to remain fastened during the whole operation of the cartridge. The interlocking means are engaged once the piston driver and the piston are fastened together.

In an embodiment of the present invention, the interlocking means are designed for preventing the rotation of the piston driver with respect to the piston in the second direction. Such interlocking means, once engaged, prevent the disconnection of the fastening means. Rotation of the interlocking means permits to rotate the rotating means and the piston driver at the same time.

If the fastening means are designed for unfastening the piston from the piston driver when the piston driver is rotated with respect to the piston in the second direction, the interlocking means thus prevent the disconnection of the fastening means. Indeed the rotation of the piston driver with respect to the piston in the second direction is not allowed when interlocking means are engaged.

In an embodiment, the invention further comprises a prismatic connection between the interlocking means and the piston driver and a clamping joint, between the rotating means and the interlocking means. Such connection permits the translation of the piston driver inside the interlocking means.

In another embodiment, when the fastening means fasten the piston with the piston driver, a translation of the piston driver in a direction along the axis A causes a translation of the piston in the same direction.

In one embodiment, the interlocking means comprises a guide bush so that once the piston driver is fastened to the piston and when the cylinder driver is coupled with the cylinder body, a rotation of the guide bush causes the simultaneous rotation of the piston driver and of the cylinder driver.

BRIEF DESCRIPTION OF THE DRAWINGS

The present invention is further illustrated by the following detailed description set forth in view of the appended drawings, which represent an exemplary and explanatory embodiment of a fluid control and processing system not restrictive of the invention, wherein:

FIG. 5a is a partial cross section view of the system showing the interlocking means interlocked with the cylinder body;

FIG. 5b is a partial cross section view of the system showing the interlocking means not interlocked with the cylinder body;

FIG. 6a is a partial cross section view of the system, when the interlocking means are interlocked with the cylinder body and the piston driver is translated along a longitudinal axis;

FIG. 6b is a partial cross section view of the system when the interlocking means are interlocked with the cylinder body

DETAILED DESCRIPTION OF THE INVENTION

Figure 1:
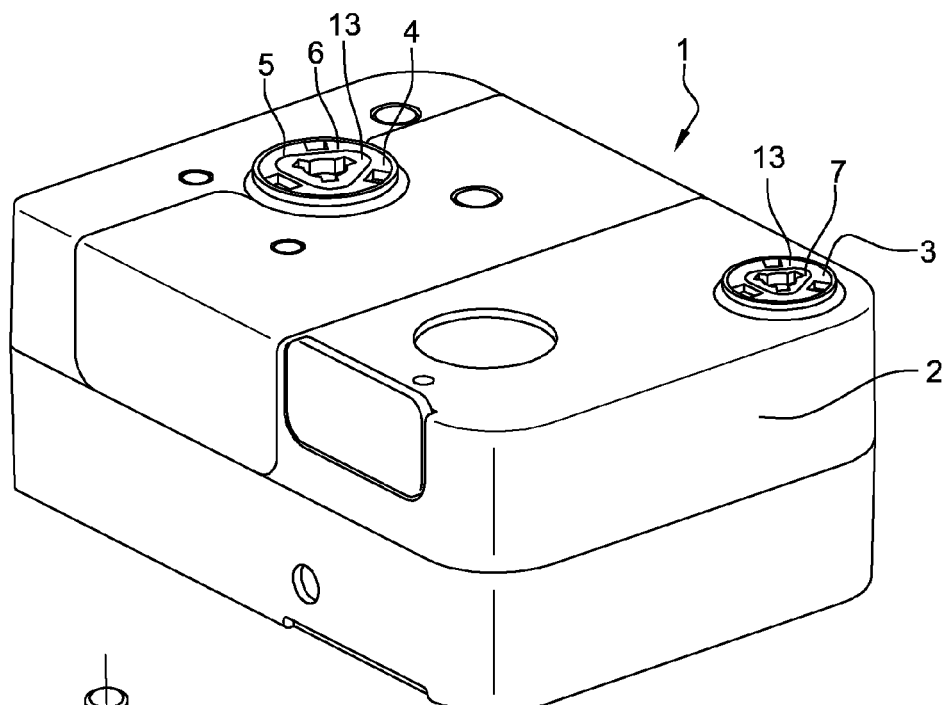
FIG. 1 illustrates a perspective view of a cartridge according to the present invention.

A fluid control and processing system 1, partially illustrated in FIGS. 1 to 7, according to the present invention comprises a cartridge 2 shown in FIG. 1. The cartridge 2 is designed for being operated by an instrument partially shown in figures. In an illustrated embodiment, cartridge 2 is adapted to receive two cylinder bodies 30. Each cylinder body 30 presents a cylinder interface 3, 4 attached to one of the extremities of the cylinder body 30, so that said cylinder interface 3, 4 is accessible from the outside of the cartridge 2. Each cylinder interface 3, 4 has a shape of a hollow right circular cylinder 5 (FIGS. 1, 3, 4, 5 and 6) presenting a circular bearing surface 6, 7 forming the external surface of said cylinder interface 3, 4. Each cylinder body 30 comprises a cylinder and at least a fluid port 34, in fluid communication with said cylinder.

The fluid control and processing system 1 further comprises dispensing ports 44, to drive at least a fluid flow. Each dispensing port 44 is positioned in order to be connectable with the fluid port 34, when the instrument is operating the cartridge 2.

Figure 2:
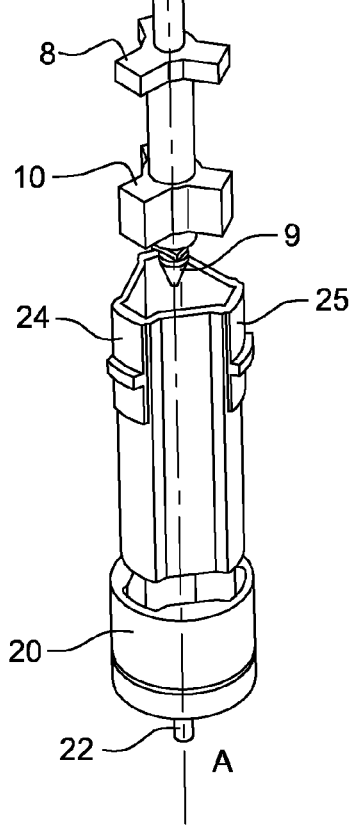
FIG. 2 is an exploded view of a piston driver from an instrument according to the present invention.
Figure 2A:
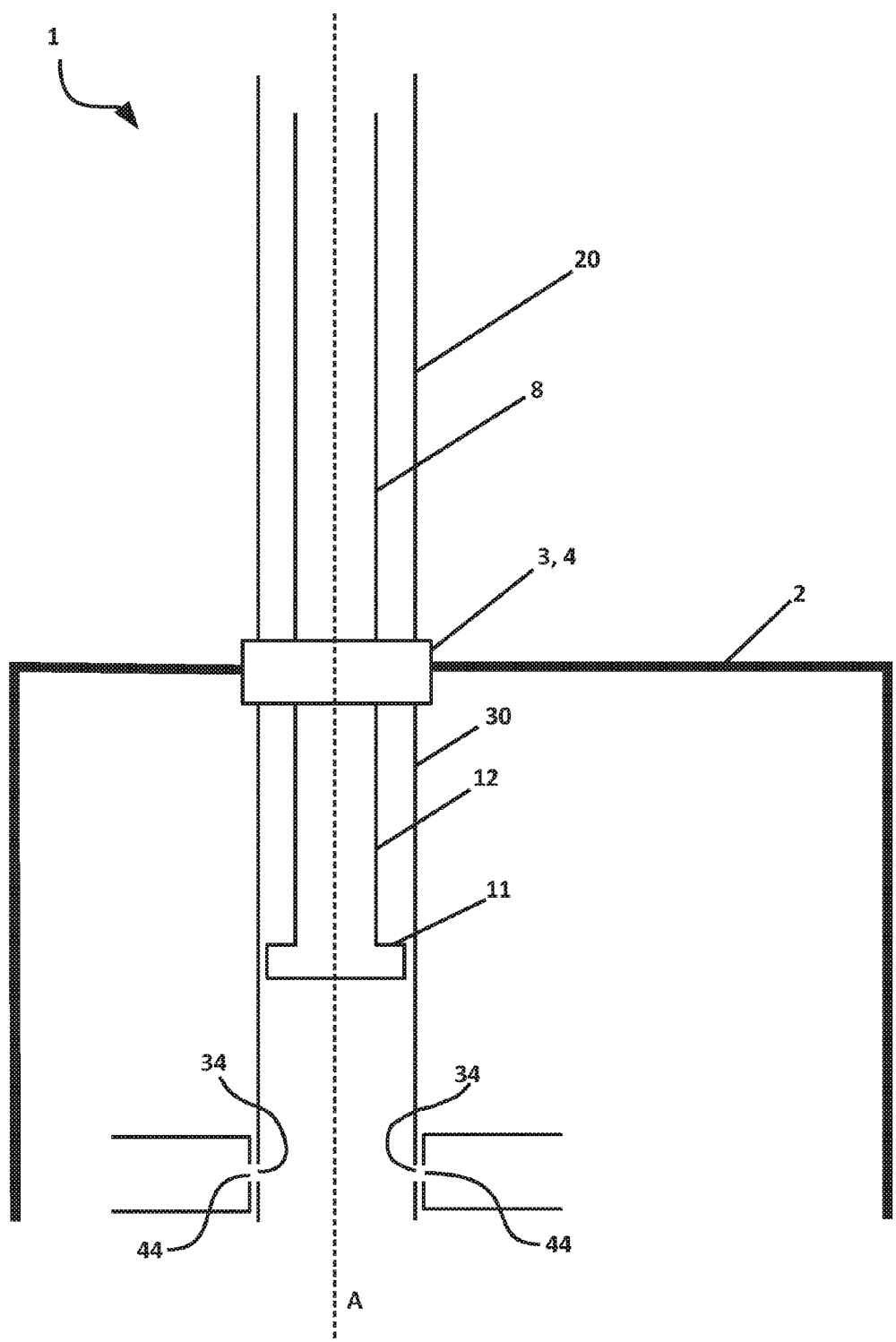
FIG. 2a is a schematic representation of a fluid control and processing system according to the present invention.
Figure 3:
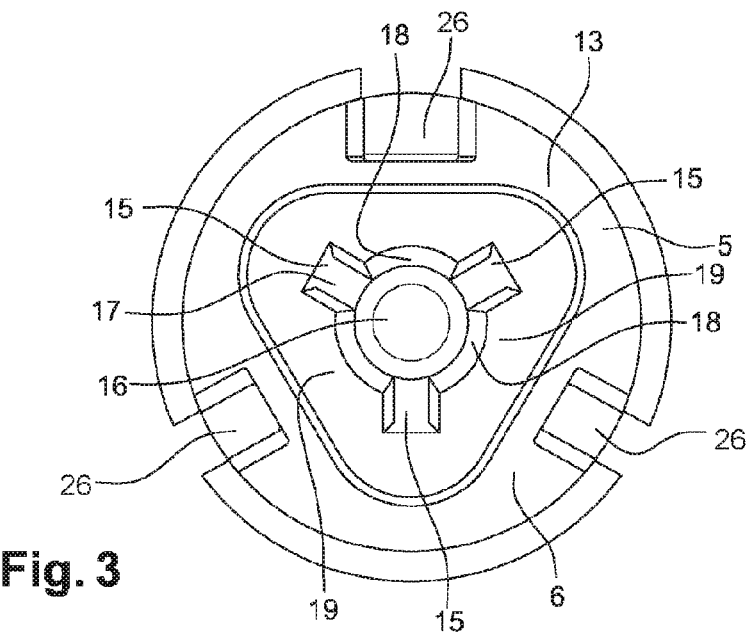
FIG. 3 is a partial cross section view of the piston received in a cylinder body.

The instrument is equipped with a piston driver 8, shown in FIG. 2, designed for operating the cartridge 2. The piston driver 8 depicted in FIG. 2 has a shape of a shaft extending along an axis A, shown in FIG. 2, and presents at one of its tips 9 three pins 10, each extending in a direction perpendicular to the axis A. Each pin 10 is evenly spaced from the other pins 10 around said axis.

The piston driver 8 is designed for driving a piston 11, partially shown in FIGS. 6a and 6b. Said piston 11 is movable in the cylinder to modulate a fluid volume inside said cylinder to draw or expel a fluid via the fluid port 34. The piston driver 8 can be connected to the piston 11 either directly (in an embodiment not shown) or via a piston rod 12 prolonging the piston 11, partially shown in FIGS. 4a, 4b, 5a, 5b, 6a and 6b. In one embodiment of the present invention, the instrument comprises two piston drivers 8 capable of respectively operating the two pistons 11. Each piston driver 8 is designed for being fastened to one piston 11 in order to move individually each piston 8 around an axis extending along the piston driver 8 fastened to each piston 11. Thus, one piston 11 is movable around an axis A (shown in FIG. 2, 2a, 4a, 4b) and the other piston is movable around an axis B (not shown in the figures).

Figure 4A:
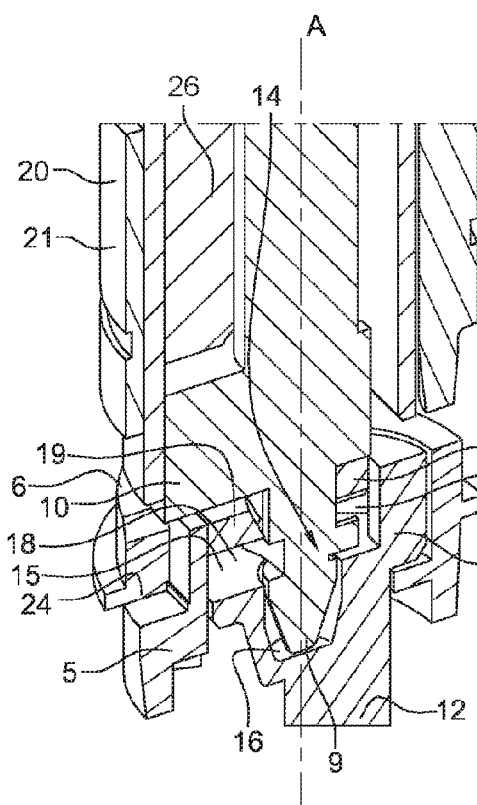
FIG. 4a is a partial cross section view of the system showing a piston driver unfastened to a piston.
Figure 4B:
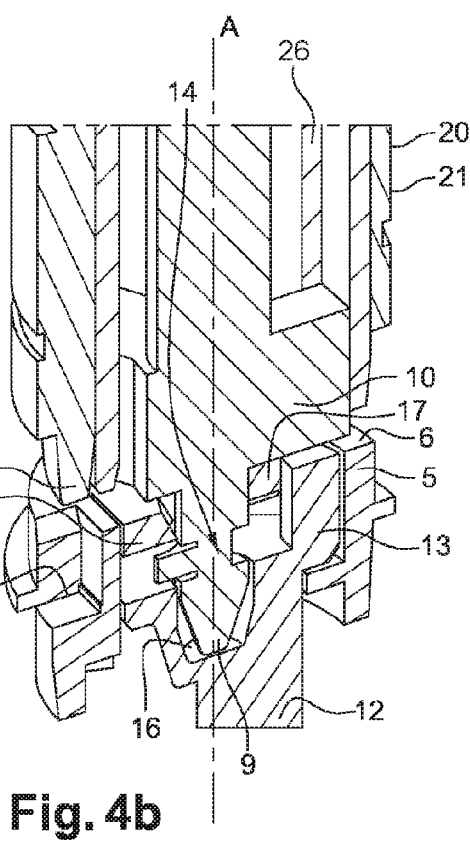
FIG. 4b is a partial cross section view of the system showing the piston driver fastened to the piston.

The fluid control and processing system 1 also includes reversible fastening means for fastening the piston 11 to the piston driver 8 in a reversible manner. Said reversible fastening means comprise at least two parts, a first part 13 located at the tip 9 of the piston rod 12 and a second part 14, complementary to the first part 13, that comprises the tip 9 and the pins 10 of the piston driver 8, as shown in FIGS. 4a and 4b.

Said fastening means form a bayonet mount as the first part 13 comprises a recess 16, adapted to receive the tip 9 of the piston driver 8, and three L-shaped grooves 15 each adapted to receive one of the pins 10. Each L-shaped groove 15 comprises a first groove 17 extending along the axis A and a second groove 18 extending in a plane that is perpendicular to said axis A, see FIGS. 3, 4a, 4b, 5a, 5b, 6a, 6b. Each second groove 18 is delineated by a rim 19 preventing a translation along the axis A of a pin 10 engaged in said second groove 18. To fasten the fastening means, the tip 9 of the piston driver 8 is inserted into the recess 16, so that each pin 10 engages in one of the first grooves 17. A rotation around the axis A in a first direction (anticlockwise in the embodiment described in the figures) of the piston driver 8 with respect to the piston 11, once the tip 9 and the pins 10 are correctly inserted in the first part 13, permits to fasten the piston driver 8 to the piston 11 as the pins 10 engage in the second grooves 18 and are blocked in translation along axis A by the rims 19. When pins 10 are in the second grooves 18, as shown in FIG. 6a, a translation of the piston driver 8 in a direction along the axis A causes a translation of the piston 11 in the same direction.

A rotation of the piston driver 8 with respect to the piston 11 in a second direction, opposite to the first direction, permits to unfasten the piston 11 and the piston driver 8.

The fluid control and processing system 1 also comprises rotating means for rotating the cylinder body 30, and thereby the fluid port 34, in order to place the fluid port 34 in fluid communication with at least one of the dispensing ports 44. Said rotating means comprise a cylinder driver 20, shown in FIGS. 4a, 4b, 5a, 5b, 6a, 6b and 7. Said cylinder driver 20 comprises a hollow circular cylindrical body 21 defining an internal space 26 whose shape is adapted to allow the piston driver 8 to translate and rotate inside. The internal space 26 presents a cylindrical shape, whose base forms substantially a triangle. The cylinder driver 20 comprises three engaging teeth 22, FIG. 7, located and designed for being inserted in complementary coupling grooves 23 located in the bearing surface 6, as shown in FIGS. 5a and 5b. When the engaging teeth 22 are inserted into said coupling grooves 23, a rotation of said cylinder driver 20 around the axis A causes a rotation of the cylinder interface 3 and of the cylinder body 30, see FIGS. 6a and 6b.

Figure 7:
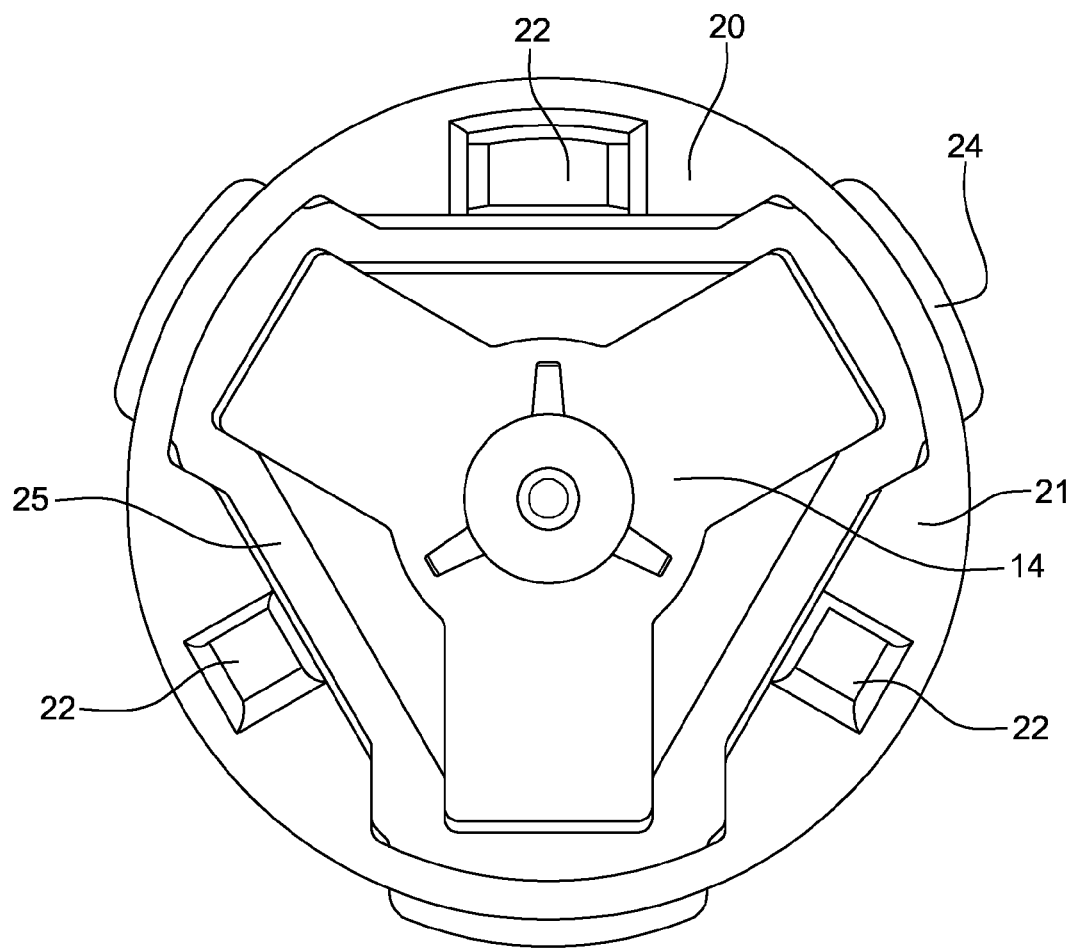
FIG. 7 is a partial cross section of the piston driver and the interlocking means.

The fluid control and processing system 1 further comprises interlocking means for interlocking the piston driver 8 and the cylinder driver 20, so that the rotation of the cylinder body 30 is controllable by the piston driver 8, when the piston driver 8 is fastened to the piston 11 by the fastening means. Such interlocking means comprises a guide bush 24 (FIGS. 2 to 7). The guide bush 24 presents a hollow extruded wall 25 whose internal section is adapted for receiving the piston driver 8 with the pins 10 as shown in FIG. 7. The external section of the extruded wall 25 is adapted to form a sliding joint with the internal space 26 of the cylinder driver 20. Once the piston driver 8 is fastened to the piston 11 and when the cylinder driver 20 is coupled with the cylinder body 30 via the cylinder interface 3, the guide bush 24 is translated along the axis A to accommodate the cylinder driver 8 and to form a joint with the cylinder driver 20 as shown in FIG. 7. In that position, a rotation of the guide bush 24 causes the simultaneous rotation of the piston driver 8 and of the cylinder driver 20.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

Having described the invention, the following is claimed:

1. A fluid control and processing system comprising:
   a cartridge;
   a cylinder body being received in the cartridge, said cylinder body comprised of a cylinder and a fluid port in fluid communication with said cylinder;
   a piston movable in the cylinder to modulate a fluid volume inside said cylinder;
   an instrument for operating the cartridge, said instrument including:
      a piston driver for driving the piston, and
      rotating means including a cylinder driver for rotating the cylinder body around an axis A which extends along the piston driver;
   dispensing ports to drive at least a fluid flow, each dispensing port being positioned to be connectable, when the instrument is operating the cartridge, with the fluid port by rotation of the cylinder body; and
   reversible fastening means for fastening the piston to the piston driver so that movement of the piston is controlled by the piston driver, wherein the reversible fastening means fastens the piston to the piston driver when the instrument rotates the piston driver with respect to the piston in a first direction around the axis A, and unfastens the piston from the piston driver when the instrument rotates the piston driver with respect to the piston in a second direction opposite to the first direction.

2. The fluid control and processing system according to claim 1, wherein the fastening means comprise at least two parts, a first part and a second part, the piston being attached to said first part and the piston driver comprising said second part.

3. The fluid control and processing system according to claim 1 wherein, when the fastening means fasten the piston with the piston driver, a translation of the piston driver in a direction along the axis A causes a translation of the piston in the same direction.

4. The fluid and control and processing system according to claim 1, wherein the cylinder driver forms a revolute joint with the cylinder body.

5. The fluid control and processing system according to claim 1, wherein the fastening means comprise a bayonet mount.

6. The fluid control and processing system according to claim 1, wherein the system further comprises:
   interlocking means for interlocking the piston driver and the rotating means, so that the rotation of the cylinder body is controllable by the piston driver, when the piston driver and the piston are fastened by the fastening means.

7. The fluid control and processing system according to claim 6, wherein the interlocking means prevents the rotation of piston driver with respect to the piston in the second direction.

8. The fluid control and processing system according to claim 6, wherein the system further comprises a prismatic connection between the interlocking means and the piston driver and a clamping joint, between the rotating means and the interlocking means.

9. The fluid control and processing system according to claim 6, wherein the interlocking means further comprises a guide bush, wherein a rotation of the guide bush causes simultaneous rotation of the piston driver and of the cylinder driver once the piston driver is fastened to the piston and when the cylinder driver is coupled with the cylinder body.

10. A cartridge comprising:
a cylinder body comprised of a cylinder and a fluid port in fluid communication with the cylinder; and
a piston movable in the cylinder to modulate a fluid volume inside the cylinder,
wherein said cartridge is used in a fluid control and processing system comprising:
an instrument for operating the cartridge, said instrument comprised of:
a piston driver for driving the piston, and
rotating means including a cylinder driver for rotating the cylinder body around an axis A which extends along the piston driver;
dispensing ports to drive at least a fluid flow, each dispensing port being positioned to be connectable, when the instrument is operating the cartridge, with the fluid port by rotation of the cylinder body; and
reversible fastening means for fastening the piston to the piston driver so that movement of the piston is controlled by the piston driver, wherein the reversible fastening means fastens the piston to the piston driver when the instrument rotates the piston driver with respect to the piston in a first direction around the axis A and unfastens the piston from the piston driver when the instrument rotates the piston driver with respect to the piston in a second direction opposite to the first direction.

11. An instrument comprising: a piston driver defining an axis A which extends along the piston driver, and a cylinder driver; wherein said instrument is used in a fluid control and processing system including: a cartridge operated by the instrument; a cylinder body being received in the cartridge and arranged to be rotated by the cylinder driver around the axis A, said cylinder body comprising a cylinder and a fluid port in fluid communication with said cylinder; a piston movable in the cylinder to modulate a fluid volume inside said cylinder, said piston driven by the piston driver; dispensing ports to drive at least a fluid flow, each dispensing port being positioned to be connectable, when the instrument is operating the cartridge, with the fluid port by rotation of the cylinder body; reversible fastening means for fastening the piston to the piston driver so that movement of the piston is controlled by the piston driver, wherein the reversible fastening means fastens the piston to the piston driver when the instrument rotates the piston driver with respect to the piston in a first direction around the axis A and unfastens the piston from the piston driver when the instrument rotates the piston driver with respect to the piston in a second direction opposite to the first direction.

* * * * *